United States Patent [19]
Grossman

[11] Patent Number: 5,126,021
[45] Date of Patent: Jun. 30, 1992

[54] LOW-VISCOSITY POLYMER SOLUTION FOR CAPILLARY ELECTROPHORESIS

[75] Inventor: Paul D. Grossman, Burlingame, Calif.

[73] Assignee: Applied Biosystems Inc., Foster City, Calif.

[21] Appl. No.: 731,771

[22] Filed: Jul. 17, 1991

[51] Int. Cl.$^5$ .................. G01N 27/26; B01D 57/02
[52] U.S. Cl. .............................. 204/180.1; 204/299 R
[58] Field of Search ..................... 204/180.1, 299 R

[56] References Cited

FOREIGN PATENT DOCUMENTS

0442177A1 8/1991 European Pat. Off. .

OTHER PUBLICATIONS

Andreas Chrambach et al "Electrophoresis on Uncrosslinked Polyacrylamide: Molecular Sieving and its Potential Applications" Electrophoresis 7 (1986) 217–220.
S. Hjertén et al "High–Performance Electrophoresis of Acidic and Basic Low–Molecular–Weight Compounds and Proteins in the Presence of Polymers and Neutral Surfactants" Journal of Liquid Chromatography 12(13)(1989) 2471–2499.
Hans–Joachim Bode "The Use of Liquid Polyacrylamide in Electrophoresis: I. Mixed Gels Composed of Agar-Agar and Liquid Polyacrylamide" Analytical Biochemistry 83 (1977), pp. 204–210.
Hans–Joachim Bode "The Use of Liquid Polyacrylamide in Electrophoresis: II. Relationship between Gel Viscosity and Molecular Sieving" Analytical Biochemistry 83 (1977) pp. 364–371.
Toshio Takagi et al "Application of Schlieren Optics to Real-Time Monitoring of Protein Electrophoresis in Crosslinker–Free Linear Polyacrylamide Solution" Electrophoresis 12(1991) pp. 436–438.
Hans–Joachim Bode "SDS-Polyethyleneglycol Electrophoresis: A Possible Alternative to SDS-Polyacrylamide Gel Electrophoresis" FEBS Letters, vol. 65, No. 1 (May 1976) pp. 56–58.
Paul M. Horowitz et al. "Electrophoresis of Proteins and Nucleic Acids on Acrylamide-Agarose Gels Lacking Covalent Crosslinking" Analytical Biochemistry 143 (1984) pp. 333–340.
Mingde Zhu et al "Factors Affecting Free Zone Electrophoresis and Isoelectric Focusing in Capillary Electrophoresis" Journal of Chromatography 480 (1989) pp. 311–319.

*Primary Examiner*—John Niebling
*Assistant Examiner*—John S. Starsiak, Jr.
*Attorney, Agent, or Firm*—Joseph Smith; Peter J. Dehlinger

[57] ABSTRACT

A capillary electrophoresis element is disclosed. The elements includes a capillary elctrophoresis tube containing a low-voscosity polymer solution having a selected mesh size and low-solution viscosity. The mesh size may range from 50–100 Å, for separating single-stranded oligonucleotides; to up to 300 Å or greater, for separating relatively large duplex DNA fragments or proteins. Also disclosed is a method for formulating a low-viscosity electrophoresis separation medium having a selected mesh size.

6 Claims, 6 Drawing Sheets

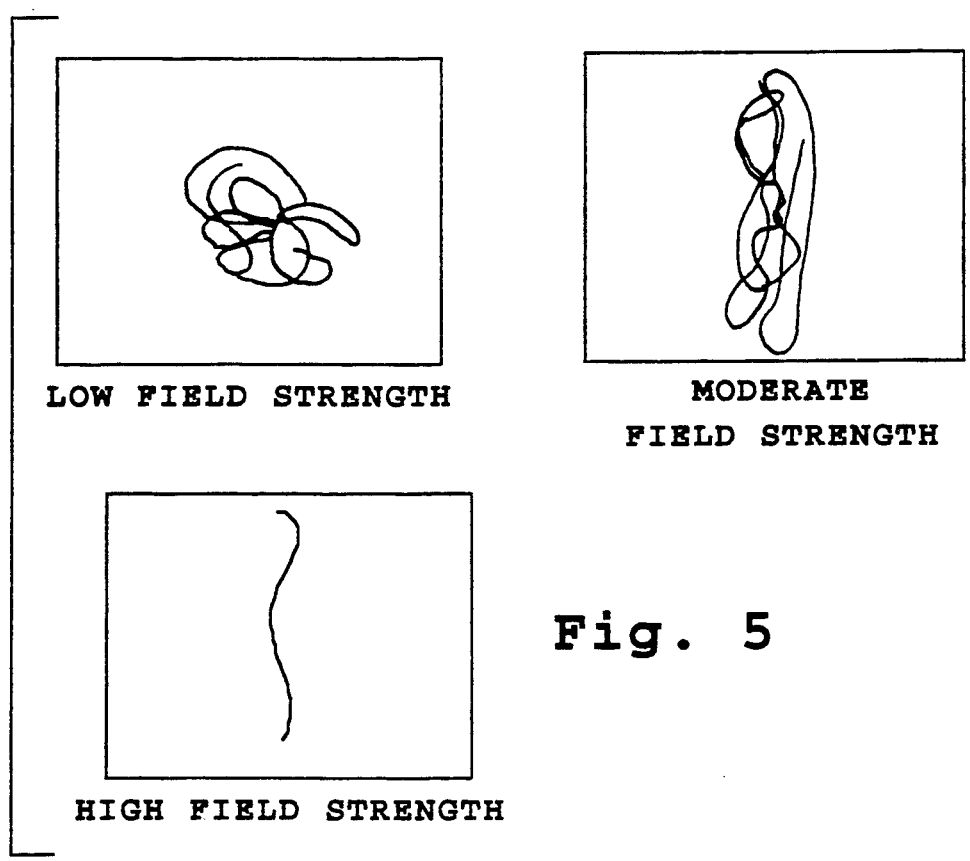
LOW FIELD STRENGTH
MODERATE FIELD STRENGTH
HIGH FIELD STRENGTH
Fig. 5
Fig. 6
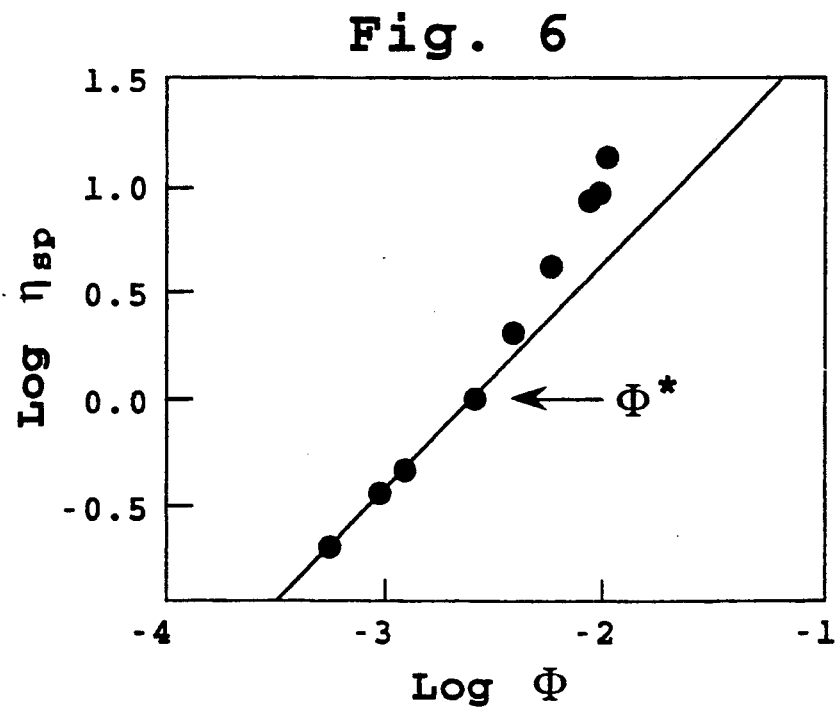

LOW-VISCOSITY POLYMER SOLUTION FOR CAPILLARY ELECTROPHORESIS

1. FIELD OF THE INVENTION

The present invention relates to capillary electrophoresis, and more particularly, to a low-viscosity polymer solution having a selected mesh size for electrophoretic separation of biopolymers.

2. REFERENCES

1. Olivera, B. M., Baine, P. and Davidson, N. (1964). *Biopolymers*, 2, 245.
2. Hermans, J. J. (1953). *J. Polymer Sci.*, 18, 257,
3. Chin, A. M. and Colburn, J. C. (1989). *Am. Biotech. Lab./News Edition*, 7, 10A.
4. Zhu, M., Hansen, D. L., Burd, S., and Gannon, F. (1989). *J. Chromator.*, 480, 311.
5. Bode, H. J. (1978). *Anal. Biochem.*, 92, 99.
6. Langevin, D. and Rondelez, F. (1978). *Polymer*, 19, 875.
7. de Gennes, P. G. (1979). "Scaling Concepts in Polymer Physics." Cornell U. P., Ithica.
8. Ogston, A. G. (1958). *Trans. Faraday Soc.*, 54, 1754.
9. Ferguson, K. A. (1964). *Metabolism*, 13, 985.
10. de Gennes, P. G. (1971). *J. Chem. Phys.*, 55, 572.
11. Doi, M. and Edwards, S. F. (1978). *JCS Faraday Transactions II*, 79, 1789–1818.
12. Lerman, L. S. and Frisch, H. L. (1982). *Biopolymers*, 21, 995.
13. Lumpkin, O. J., Dejardin, P. and Zimm, B. H. (1985). *Biopolymers*, 24, 1573.
14. Hervet, H, and Bean, C. P. (1987). *Biopolymers*, 26, 727.
15. Schwartz, D. C., Saffran, W,, Welsh, J., Haas, R., Goldenberg, M. and Cantor, C. R. (1982). *Cold Spring Harbor Symp.*, 47, 189.
16. Jorgenson, J. N. and Lukacs, K. D. (1983). *Science*, 222, 266.
17. Lauer, H. H. and McManigill, D. (1986). *Anal. Chem.*, 58, 166.
18. Grossman, P. D., Colburn, J. C. and Lauer, H. H. (1989). *Anal. Biochem.*, 179, 28.
19. Rodrigues, F. (1982). "Principles of Polymer Systems." McGraw Hill, N.Y.
20. .Hill, D. A. and Soane, D. S. (1989). *J. Polym. Sci. Poly. Phys.*, B27, 2295.
21. Allcock, H. R. and Lampe, F. W. (1981). "Contemporary Polymer Chemistry." Prentice-Hall, Englewood Cliffs.
22. Brandrup, J. and Immergut, E. H. (1989). "Polymer Handbook 3rd Edition." John Wiley & Sons, N.Y.
23. Flory, P. J. (1953). "Principles of Polymer Chemistry." Cornell U.P., Ithaca.
24. Righetti, P. G., Brost, B. C. W. and Snyder, R. S. (1981). *J. Biochem. Biophys. Methods*, 4, 347.
25. Cantor, C. R. and Schimmel, P. R. (1980). "Biophysical Chemistry." W. H. Freeman, N.Y.
26. Slater, G. W., Rousseau, J., Noolandi, J., Turmel, C. and Lalande, M. (1988). *Biopolymers*, 27, 509.
27. Slater, G. W. and Noolandi, J, (1989). *Biopolymers*, 28, 1781,

3. BACKGROUND OF THE INVENTION

It is well known that, for many charged biopolymers of interest, e.g., single- and double-stranded DNA and sodium dodecyl sulfate (SDS)-denatured proteins, separations based on differences in electrophoretic mobilities in free solution are not possible [1,2]. Therefore, in order to effect electrophoretic separations of mixtures of these molecules, one has to employ a gel matrix which alters the frictional characteristics of these species in such a way as to introduce a molecular size dependence to electrophoretic mobility.

Heretofore, the gel matrix employed in capillary electrophoretic systems has generally been a solid gel, such as agarose gel, or cross-linked polymer matrix, such as a cross-linked polyacrylamide matrix. Such gels may be difficult to introduce into a capillary tube without bubbles or voids, and generally preclude reusing the tube.

More recently, capillary electrophoresis systems employing a polymer solution as separation medium have been disclosed. Co-owned U.S. patent application for "Nucleic Acid Fractionation by Counter-Migration Capillary Electrophoresis", Ser. No. 390,631, describes an electrophoresis system in which DNA fractionation occurs in a polymer solution which itself is migrating through the tube, by electro-osmotic flow, in a direction opposite to that of DNA movement in the gel. Co-owned U.S. patent application for "High-Viscosity Polymer Matrix and Methods", Ser. No. 472,045 discloses the use of a viscoelastic polymer solution as a substitute matrix for a cross-linked gel matrix in capillary electrophoresis.

Ideally, a polymer solution for separating a mixture of biopolymer molecules (e.g., DNA fragments or polypeptides) should have a selected mesh size for optimizing separation of the biopolymer molecules, and at the same time, have a minimum viscosity, to allow the solution to be readily drawn into and removed from the capillary tube. Heretofore, selecting polymers and polymer concentrations which provide a selected mesh size and low viscosity has been difficult. In particular, small mesh sizes suitable for fractionation of oligonucleotides, e.g., in DNA sequencing, has generally been achieved only at high polymer concentrations which also produce high solution viscosity. At the other end of the mesh size spectrum, where large polymers are required for achieving large mesh sizes, even relatively dilute polymer solutions can have relatively high viscosities.

4. SUMMARY OF THE INVENTION

The present invention, includes, in one aspect, a capillary electrophoresis element. The element includes an electrophoresis tube, and contained within the tube, a solution of an uncharged, water-soluble polymer characterized by:

(a) a polymer mass concentration C which is between about $1[\eta]$ and $5[\eta]$, where $[\eta]$ is the intrinsic viscosity of the polymer;

(b) an actual solution viscosity of less than about 100 centipoise; and (c) a polymer mesh size $\xi$ which is approximately equal to $aC^{-0.75}$, where a is the persistence length of the polymer.

In one embodiment, in which the polymer solution has a mesh size between about 50 and 150 Å the mass concentration of the polymer is between about 3 and 6 weight percent, and the polymer solution has a viscosity between about 5 and 50 centipoise. In another embodiment, in which the mesh size is between about 200 and 300 Å, the mass concentration of the polymer is between about 0.2 and 0.6 weight percent, and the polymer solution has a viscosity between about 1 and 10 centipoise.

In another aspect, the invention includes a method of preparing a polymer element for use in electrophoretically separating, by capillary electrophoresis, a mixture of biopolymer molecules within a selected size range. The method includes the steps of, first selecting a polymer mesh size suitable for separating the biopolymer mixture, in an electric field, and then selecting an uncharged, water-soluble polymer having an intrinsic viscosity [$\eta$] and a persistence length a, such that and the selected mesh size is approximately equal to $aC^{-0.75}$, where C is between about $1//[\eta]$ and $5/[\eta]$. There is formed a solution of the polymer at a concentration C between about $1//[\eta]$ and $5/[\eta]$, and this solution is drawn into a capillary electrophoresis tube.

These and other objects and features of the invention will become more fully apparent when the following detailed description of the invention is read in conjunction with the accompanying drawings.

BRIEF DESCRIPTION OF THE DRAWINGS

FIG. 5 is a schematic illustration showing the elongational influence of the electric field on the size of a molecule migrating by the reptation mechanism when $E=0$, $R_g\sim N^{0.5}$ and $\mu\sim 1/N$, whereas for large E, $R_g\sim N^{1.0}$, and $\mu$ is independent of N;

FIG. 6 shows the dependence of the specific viscosity, $\eta_{sp}$, of an HEC-buffer solution on HEC concentration;

DETAILED DESCRIPTION OF THE INVENTION

I. Polymer Mesh Size and Viscosity Considerations

A. Polymer Mesh Size

In this section the concept of an entangled polymer solution and some of the scaling laws which have been developed to describe their properties are presented.

Figure 1A:
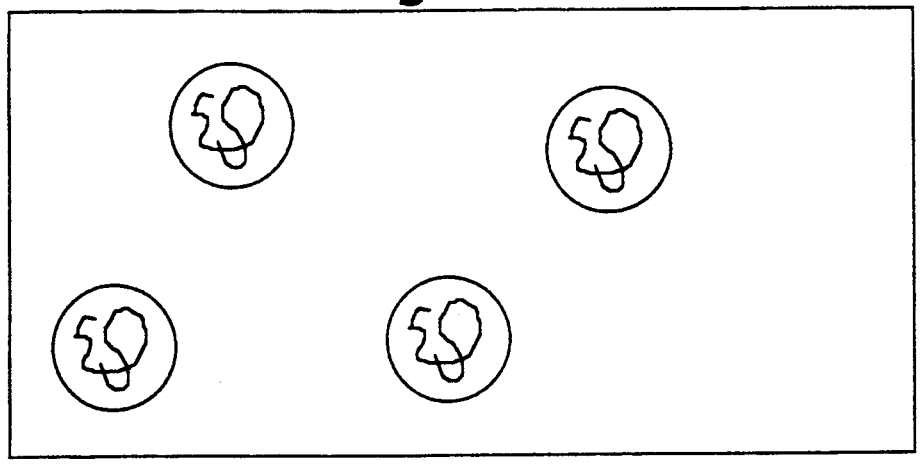
FIG. 1 is a schematic representation of the entanglement process, where in frame A, $\Phi<\Phi^*$, in frame B, $\Phi\approx\Phi^*$ and in frame C, $\Phi>\Phi^*$.
Figure 1B:
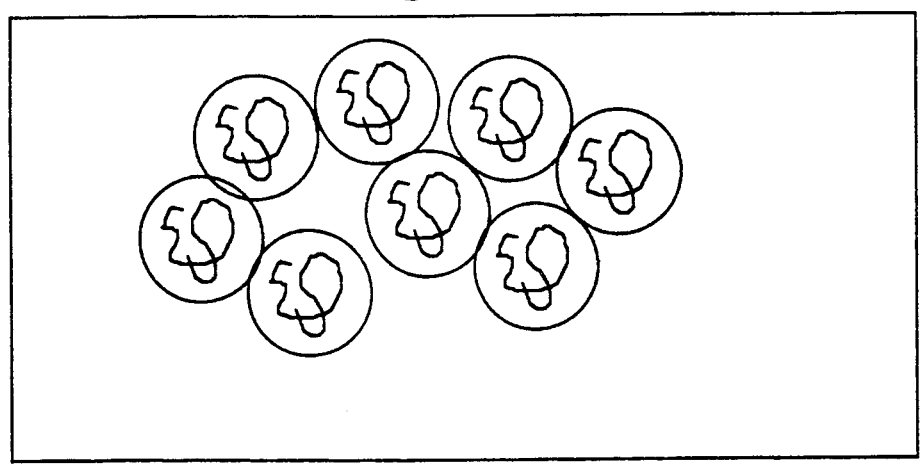
Figure 1C:
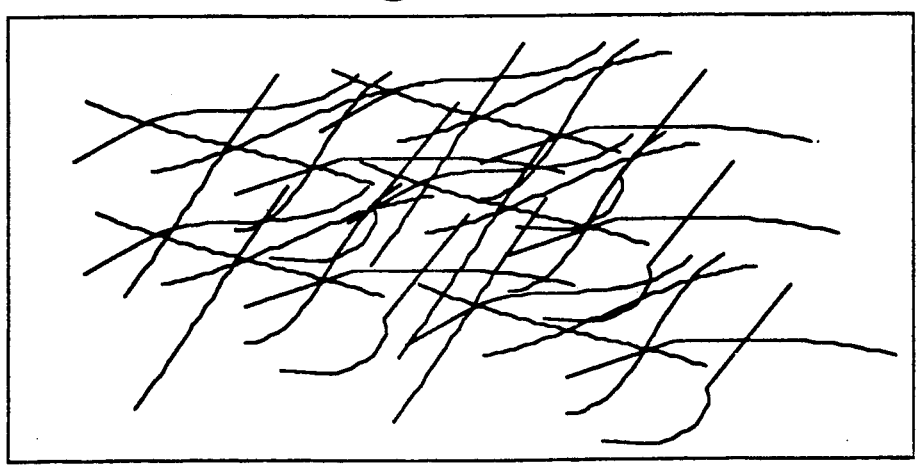

Overlap Threshold: An important difference exists between polymer solutions which are dilute, where the polymer chains are hydrodynamically isolated from one another, and more concentrated solutions, where the chains overlap and interact. The polymer volume fraction at which the polymer chains begin to interact with one another, $\Phi^*$, is called the overlap threshold. Above this concentration, the solution is said to be entangled. A schematic illustration of the entanglement process is given in FIG. 1.

An expression predicting the value of $\Phi^*$ as a function of polymer size was first derived by de Gennes [7]. This expression is based on the assumption that when $\Phi\approx\Phi^*$, the bulk concentration of the solution is the same as the concentration inside a single coil. For polymers in an athermal solvent, this assumption leads to the expression $$\Phi^*\approx N^{-0.8} \tag{1}$$

Note that if N is large, $\Phi^*$ can be very small. For example, if $N=10^4$, $\Phi^*$ is on the order of $10^{-3}$. Thus, even seemingly dilute polymer solutions can be in an entangled state.

Figure 2:
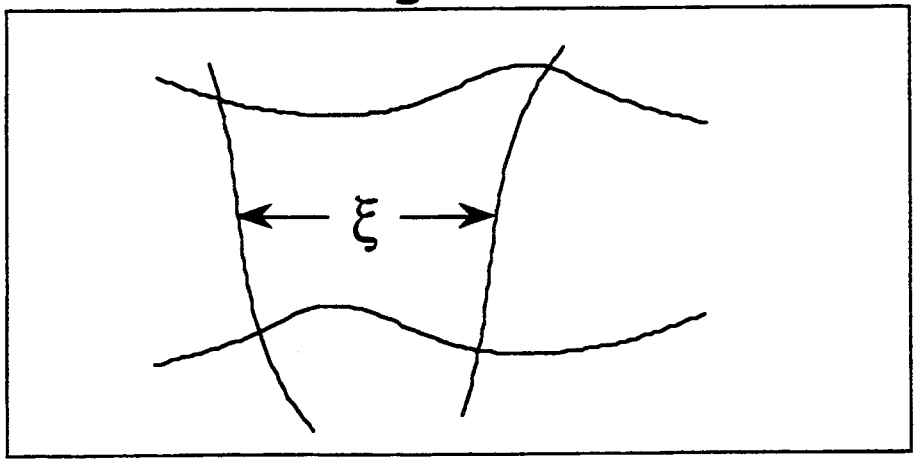
FIG. 2 is a schematic illustration of the entangled mesh, where $\xi$ indicates the size of the mesh.

An entangled solution is characterized by an average mesh size, $\xi$ (FIG. 2). de Gennes [7] has derived an approximate expression relating $\xi$ to the polymer volume fraction, $\Phi$, for $\Phi>\Phi^*$, $\xi$ depends only on the volume fraction of the polymer, $\Phi$, and not on the size of the polymer chain, N. This simply states that the mesh size is smaller than the overall length of the polymer. Next, it is assumed that when $\Phi\approx\Phi^*$, the mesh size is comparable with the size of an individual coil, $R_g$. These two assumptions lead to the expression $$\xi(\Phi)\approx a\Phi^{-0.75} \tag{2}$$

Again, Eq. (2) assumes that the polymer is dissolved in an athermal solvent. This is an important result tying the size of the mesh in an entangled solution to the volume fraction of polymer.

B. Optimum Polymer Size

In order to apply entangled polymer solutions to the widest range of biopolymer separations, one wants to be able to vary the mesh size in the solution. But, according to Eq. (2), if one wants to form a small mesh, for a given polymer, one must use a high concentration of polymer. However, as the polymer concentration is increased, so is the solution viscosity. Ideally, one would like to maintain the practical advantages of a low viscosity when going to a smaller mesh. The above relationships give an indication of how this might be accomplished. In order to minimize the viscosity of the polymer solution, one wants to operate near $\Phi^*$. But, Eq. (2) predicts that, in order to achieve a small mesh, one needs a large value of $\Phi$. To satisfy both constraints, one should use a shorter polymer to form a tighter mesh. This can be demonstrated by combining Eqs. (1) and (2) to give the expression, $$\xi(\Phi^*) \approx a\, N^{0.6} \tag{3}$$

Thus, to create a larger mesh while minimizing the viscosity of the solution, one wants to use a longer polymer and to create a smaller mesh one wants to use a shorter polymer.

C. Electrophoretic Migration

Once the network structure of the polymer solution has been established, we can address the effects of the polymer-solution network on electrophoresis. As is the case for traditional gel electrophoresis, two main theories exist which describe the migration of a flexible macromolecule through a polymer network: the Ogston sieving model and the reptation model The applicability of each depends on the size of the migrating molecule relative to the mesh size of the network.

Figure 3:
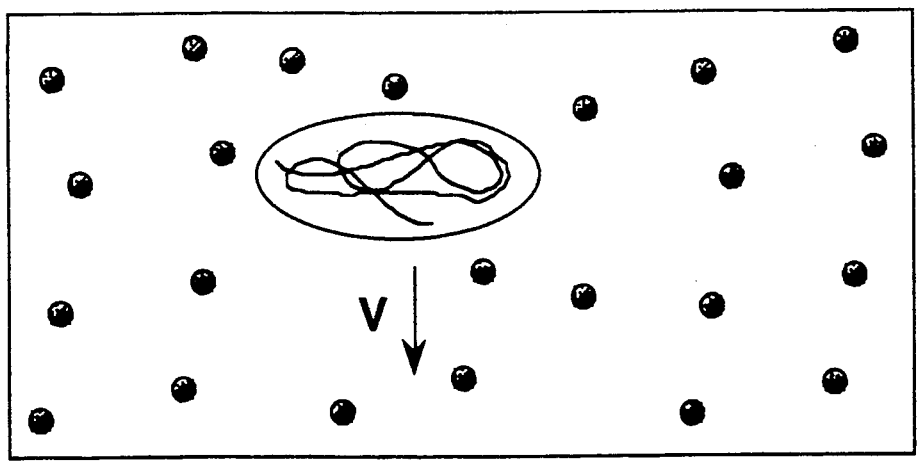
FIG. 3 is a schematic diagram of a solute migrating through a polymer network by the Ogston mechanism in which the solute percolates through the mesh as if it were a rigid particle.

The Ogston Model: The Ogston model treats the polymer network as a molecular sieve. It assumes that the matrix consists of a random network of interconnected pores having an average pore size, $\xi$, and that the migrating solute behaves as an undeformable particle of radium $R_g$. According to this model, smaller molecules migrate faster because they have access to a larger fraction of the available pores. The mathematical treatment of this problem was first presented by Ogston [8]. FIG. 3 is a schematic illustration showing a solute migrating through a polymer network by the Ogston mechanism.

In the Ogston theory, the electrophoretic mobility of the migrating solute through the porous structure is assumed to be equal to its free solution mobility, $\mu_0$, multiplied by the probability that the solute will meet a pore large enough to allow its passage. Thus $$\mu = \mu_0 P\,(\xi \geq R_g) \tag{4}$$

where $\xi$ is the radius of the pore in which the coil resides, and $P(\xi \geq P_g)$ is the probability that a given pore has a radius greater than or equal to the radius of the migrating particle. The Ogston model of the pore size distribution predicts that, in a random network of linear polymers, the fraction of pores large enough to accommodate a spherical particle of radius $R_g$ is $$P(\xi \geq R_g) = exp(-\pi n l (r+R_g)^2) \tag{5}$$

where n is the average number of polymer strands per unit volume, 1 is the average length of the polymer strands, and r is the thickness of the strands. Furthermore, this model assumes that the product n*1 is proportional to the concentration of the gel-forming polymer, C. Thus, $$P(\xi \geq R_g) = exp(-KC(r+R_g)^2) \tag{6}$$

where K is a constant of proportionality. In Eq. (6), the term $K(r+R_g)^2$ is known as the retardation coefficient, $K_r$, and is a characteristic of a given molecular species in a particular polymer system.

Combination of Eqs. (4) and (6), gives the final expression describing the migration of a solute through a polymer network according to the Ogston mechanism, $$\mu = \mu_0 exp(-KC(r+R_g)^2) \tag{7}$$

Note that if $r<<R_g$, one would expect that a plot of $\log(\mu/\mu_0)$ vs C would give a straight line with a slope proportional to $R_g^2$. Such plots are known as Ferguson plots [9].

As stated before, the Ogston model assumes that the migrating solute behaves as an undeformable spherical particle. It does not take into account the fact that the migrating molecule might deform in order to "squeeze" through a pore. Therefore, when $R_g > \xi$, the Ogston model predicts that the electrophoretic mobility of the migrating solute will rapidly approach zero. However, it is well known that large flexible chain molecules such as DNA continue to migrate even when $R_g >> \xi$. This is explained by the second model for migration, the reptation model. The reptation model assumes that instead of migrating as an undeformable particle with radius $R_g$, the migrating molecule moves "head first" through the porous network. The reptation model is the subject of the following section.

Figure 4:
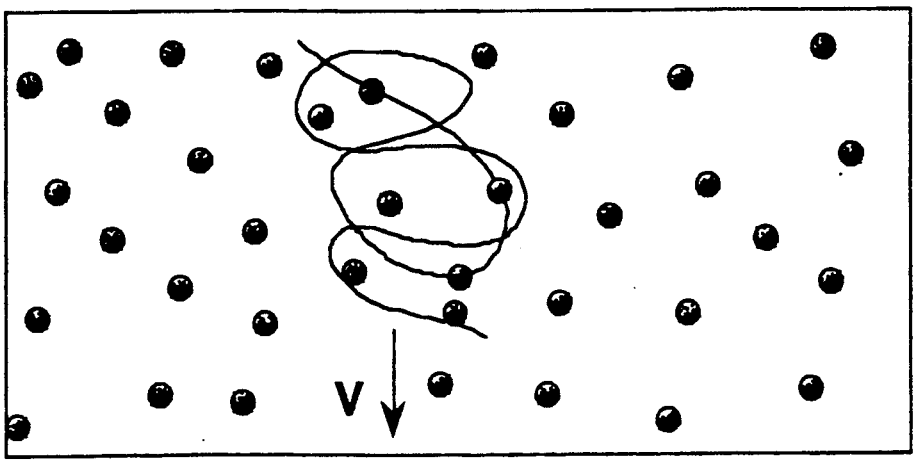
FIG. 4 is a schematic diagram of a solute migrating by the reptation mechanism in which the solute coil is forced to squeeze "head first" through the "tubes" formed by the polymer network.

Reptation and Biased Reptation: The basis of the reptation model is the realization that when a long flexible molecule travels through a polymer network having a mesh size smaller than $R_g$ it does not necessarily travel as an undeformed particle, but rather "snakes" through the polymer network "head first." The migrating solute is assumed to be confined to "tubes" which are formed by the gel matrix. The term reptation comes from the reptile-like nature of this motion. FIG. 4 shows a schematic illustration of a flexible macromolecule undergoing reptation. The first description of the reptation mechanism was presented by de Gennes [7,10] and Doi and Edwards [11], while the first application of reptation theory to the electrophoresis of biopolymers was presented by Lerman and Frisch [12]. According to these models, when a flexible solute is migrating by the reptation mechanism, in the limit of zero electric field strength, $$\mu \sim \frac{N_2}{N} = \frac{1}{N} \tag{8}$$

Eq. (8) states that for a chain-like molecule undergoing reptile motion under the influence of an electric field, the electrophoretic mobility is inversely proportional to the molecular length.

A refinement on the reptation model which takes into account the influence of large electric fields is the biased-reptation model. When the electric field becomes large, the assumption that the migrating molecule exists as an unperturbed coil, is no longer valid. Because of the induced orientation of the larger segment, as the field strength is increased, the coil becomes more elongated. This is shown schematically in FIG. 5. In the limiting case, the coil becomes a rod. If the migrating molecule becomes a rod the electrophoretic mobility again becomes independent of molecular size. Thus, as the coil becomes more elongated, the size 1/N dependence of $\mu$ disappears. This effect was first described by Lumpkin [13] who arrived at an expression of the form $$\mu \approx K\left(\frac{1}{N} + bE^2\right) \tag{9}$$

where K is a constant and b is a function of the mesh-size of the polymer network as well as the charge and persistence length of the migrating solute. Note that the first term in Eq. (9) depends on the size of the migrating molecule but does not depend on the electrical field strength, while the second term does depend on molecular size but does not depend on electrical field strength. Therefore, as the electrical field or the molecular size increases, the dependence of mobility on molecular size decreases. This is the key prediction of the biased reptation model. The predicted behavior has been observed experimentally [14]. Because of this effect, the maximum size of DNA which can be separated using traditional electrophoretic techniques is approximately 20,000 base-pairs. To go beyond this limit pulsed-field techniques must be used.

II. Polymer Selection Method

In accordance with one aspect of the invention, there is provided a method of preparing a polymer element for use in electrophoretically separating, by capillary electrophoresis, a mixture of biopolymer molecules within a selected size range. Initially in the method, one selects a polymer mesh size $\xi$ suitable for separating the biopolymer mixture in an electric field. For example, for separating single-stranded oligonucleotides, a mesh size between about 50–150 Å is suitable. For separating relatively large duplex DNA, e.g., in the size range up to 10 kilobasepairs, a mesh size of 200–300 Å is suitable.

There is then selected an uncharged, water-soluble polymer having an intrinsic viscosity $[\eta]$ and a persistence length a, such that and the selected mesh size is approximately equal to $aC^{-0.75}$, where C is between about $1//[\eta]$ and $5/[\eta]$, and the actual viscosity is less than about 100 centipoise.

Preferred polymers for use in the present invention are linear polyoxides, polyethers, such as polyethylene oxide (polyethyleneglycol), and polypropylene oxide, polyethylene imine, polyacrylic acid, polycrylamide, polymethacrylamide, polymethacrylic acid, polyvinylacetate, polyvinylpyrrolidone, polyvinyloxazolidone, and a variety of water-soluble hydroxyl polymers, such as natural gums (xanthan, dextran, guar, etc.), water-soluble cellulose compounds, such as methylcellulose and hydroxyethylcellulose, and co-polymers and blends of these polymers.

Suitable water-soluble polymers having a wide range of molecular weights (often expressed in terms of solution viscosity, at a given polymer concentration) are available commercially, or can be prepared under defined polymer formation conditions, as illustrated in the examples below.

The intrinsic viscosity of a polymer can be determined experimentally as follows. The specific viscosity $\eta_{sp}$ of a solution is first measured, at a selected temperature (the expected run temperature of the electrophoresis) from the actual viscosity $\eta_a$ of the solution and the viscosity of the solvent $\eta_o$, from the expression $\eta_{sp} = \eta_a/\eta_o - 1$. When the expression specific viscosity/polymer concentration ($\eta_{sp}/C$) is plotted against polymer concentration, the Y intercept (zero polymer concentration) gives the intrinsic viscosity $[\eta]$ on the $\eta_{sp}/C$ axis.

As discussed below, the entanglement concentration of a selected polymer occurs at a concentration C* at which $C^*[\eta] = 1$, that is, where $C = 1/[\eta]$ Thus, a polymer concentration between about $1/[\eta]$ and $5/[\eta]$ extends from the entanglement concentration C to a concentration 5 times C*. Preferably, the polymer concentration is between C* and 2C*.

The polymer persistance length a can be determined from the intrinsic viscosity $[\eta]$, molecular weight (MW), the constant $\Phi_c$, and $<r^2>$, according to equations 11 and 12 below. Once the value of a is known, the mesh size of the polymer can be determined from equation (2), as above.

The lower range of the polymer concentration (C*) is that just necessary to produce the requisite entanglement in the polymer. The upper range of polymer (e.g., 2–5C*) decreases mesh size, according to equation (2), but still ensures a low viscosity of the polymer solution, preferably less than about 100 centipoise, and more preferably between about 1–50 centipoise.

By way of illustration, to prepare a low-viscosity solution with a mesh size of between about 50–150 Å, a hydroxyethylcellulose (HEC) polymer (which has an a value of about 4.25 Å) and having a molecular weight of about 24 kilodaltons (N=about 128) is formulated in an aqueous buffer to a final polymer concentration between about 3 and 6 weight percent. The viscosity of the solution is between about 5 and 50 centipoise. This solution is suitable for electrophoretic separation of single-stranded oligonucleotides.

Similarly, to prepare a polymer solution having a mesh size of between about 200 and 300 Å, a hydroxyethylcellulose (HEC) polymer having a molecular weight of about 19 kilodaltons (N is about 1026) is formulated in an aqueous buffer to a final polymer concentration between about 0.2 and 0.6 weight percent. The viscosity of the solution is between about 1 and 10 centipoise. This solution is suitable for electrophoretic separation of duplex DNA fragments having molecular weights up to about 10 kilobp.

After preparing the polymer solution with the selected mesh size and desired low viscosity, the solution is drawn into a capillary tube for use in electrophoretic separation of biopolymers. Electrophoretic separation may be carried out according to standard capillary electrophoresis methods.

III. Capillary Electrophoresis Element

In another aspect, the invention includes a capillary electrophoresis element. The elements is prepared as described in Section II and includes a capillary electrophoresis tube, and contained within the tube, a solution of an uncharged, water-soluble polymer characterized by:

(a) a polymer mass concentration C which is between about $1[\eta]$ and $5[\eta]$ where $[\eta]$ is the intrinsic viscosity of the polymer;

(b) an actual solution viscosity less than about 100 centipoise; and (c) a polymer mesh size which is approximately equal to $aC^{-0.75}$, where a is the persistence length of the polymer.

In one exemplary embodiments, prepared as above, the the mesh size is between about 50 and 100 Å, the mass concentration of the polymer is between about 3 and 6 weight percent, and the polymer solution has a viscosity between about 5 and 50 centipoise. In another exemplary embodiment, also prepared as as described in Section II, the mesh size is between about 200 and 300 Å, the mass concentration of the polymer is between about 0.2 and 0.6 weight percent, and the polymer solution has a viscosity between about 1 and 10 centipoise.

The following methods and examples illustrate various preparations and methods employed in practicing the present invention. The examples are intended to illustrate, but not limit the scope of the invention.

EXAMPLE 1

Experimental Methods

A. Capillary Electrophoresis System

The capillary electrophoresis system used in this work closely resembles that described elsewhere [16,17]. A straight length of polyimide-coated fused silica capillary (Polymicro Technologies Inc., Phoenix, Ariz.), 50 cm (35 cm to the detector) long with 50 μm internal diameter and a 375 μm outside diameter, connects the anodic reservoir with the electrically grounded cathodic reservoir. A high voltage power supply capable of producing up to 30,000 V (Gammar High Voltage Research, Inc., Ormand Beach, Fla.) was used to drive the electrophoretic process. Current through the capillary was measured over a 1kΩ resistor in the return circuit of the power supply using a digital multimeter (Hewlett-Packard, Model 3465B, Palo Alto, Calif.).

On-column uv detection at 260 nm was carried using a modified variable wavelength detector (Applied BioSystems, Model 783. Foster City, Calif.). The electrophoresis system was enclosed in an insulated compartment having safety interlocks in order to prevent electric shock. Data was collected using an integrator (Hewlett Packard, Model 3390A, Palo Alto, Calif.). Samples were introduced into the capillary by applying a vacuum of 5 in Hg to the cathodic electrode reservoir for between 2 and 3 seconds while the anodic end of the capillary was immersed in the sample solution. After the sample slug was introduced into the capillary, the anodic end of the capillary was then placed back into the electrophoresis buffer along with the anodic electrode, and the electrophoretic voltage was then applied. The temperature of the agitated air surrounding the capillary was maintained at 30.0° C.±0.1° C. for all experiments. A description of the methods used to calculate electrophoretic mobilities is provided elsewhere [18].

B. Viscosity Measurements

Viscosity measurements were performed using an ostwald viscometer [19] thermostated in a water batch at 30° C.±0.5° C.

The DNA mixture used in this study was a commercially prepared restriction digest of the ΦX174 plasmid (Bethesda Research Labs, Md.). The buffer used in all experiments was 89 mM tris [hydroxymethyl]aminomethane, 89 mM boric acid and 5 mM ethylenediaminetetraacetic acid (TBE) with varying amounts of added (hydroxyethyl) cellulose (HEC).

EXAMPLE 2

Entanglement Threshold and Mesh-Size of HEC Solutions

A. Entanglement Concentration

Experimentally, the point at which a polymer solution becomes entangled can be determined by plotting the log for the specific viscosity, $\eta sp$, as a function of polymer volume fraction [20]. For independent, non-interacting polymer molecules, i.e., $\Phi < \Phi^*$, dilute solution theories predict that the slope of such a curve should be approximately 1.0 [21]. Then, as the polymer coils begin to interact, the slope is expected to increase. As an example of this behavior, experimental results are presented in FIG. 6 for solutions of hydroxyethyl cellulose (HEC) dissolved in a tris-borate electrophoresis buffer. The solid line in FIG. 6 is the least-squares fit to the first 4 points, where the slope is 1.07. These data imply that, for this system, $0.29\% < \Phi^*_{HEC} < 0.4\%$. It is significant that the absolute value of the viscosity of this HEC solution at the entanglement threshold is very low—on the order of 1 centipoise (cp). This is one of the most striking features of these systems; that one can create a network structure in solutions having the viscosity of water.

To check the agreement between the experimental value of $\Phi^*$ found in FIG. 6 and that predicted by Eq. (1), we must first determine an approximate value for N for the HEC. This can be done using the Mark-Houwink-Sakurada equation [22], $$[\eta] = K^* (MW)^{aMHS} \tag{10}$$

where $[\eta]$ is the intrinsic viscosity, MW is the polymer molecular weight and K and aMHS are constants characteristic of a given polymer/solvent system at a given temperature. For HEC dissolved in water, $K = 9.533 * 10^{-3}$ ml/g and aMHS=0.87 [22]. From viscosity measurements (data not shown), the value of $[\eta]$ and the parameters K and aMHS we can determine an approximate value for the polymer molecular weight. The resulting value for the molecular weight of the HEC is 191,800. Thus, the value of N is 1026, assuming a monomer molecular weight of 187 for HEC. With this value of N, Eq. (1) predicts $\Phi^*_{HEC} = 0.39\%$; in good agreement with the experimental value of $0.29 < \Phi^*_{HEC} = 0.40$.

B. Mesh Size

In order to apply Eq. (2) to calculate a mesh size, we must first estimate a value for the statistical segment length, a, for HEC. The value of a can be estimated using intrinsic viscosity measurements. From Flory [23], for a random-coil polymer, $$[\eta] = \frac{\Phi_c \langle r^2 \rangle^{\frac{3}{2}}}{MW} \tag{11}$$

where $\Phi_c$ is a universal constant having a value of $2.1*10^{23}$ if $[\eta]$ has the units of ml/g and $<r^2>$ is the root mean squared end-to-end distance between the ends of the polymer chain Furthermore, for an unperturbed chain, $$\langle R_g^2 \rangle = \frac{\langle r^2 \rangle}{6} \tag{12}$$

Based on a measured value of 317 ml/g for $[\eta]$ in the electrophoresis buffer (data not shown), Eq. (11) and (12) give a value of 270 Å for $R_g$. Next, given the relationship between the segment length, a, and $R_g$ for an unperturbed coil, $$R_g = aN^{0.6} \tag{13}$$

and given that N=1026, we can see that a=4.21Å. This is close to the published 4.25Å segment length for HEC [22]. This value of a is currently being confirmed in this laboratory using dynamic light scattering measurements.

Figure 7:
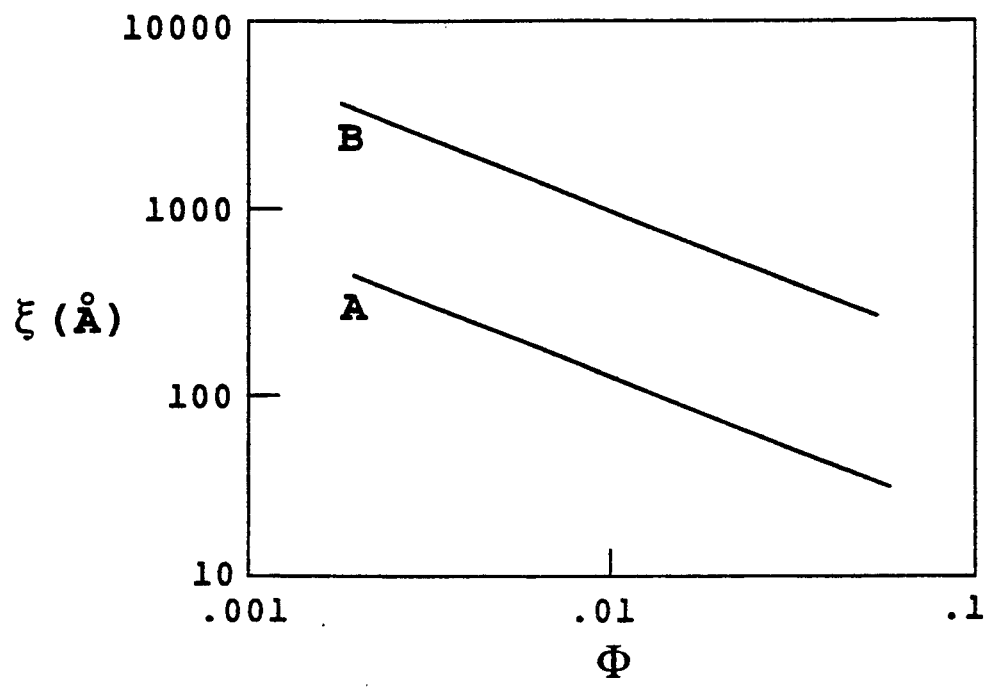
FIG. 7 presents curves showing the mesh size, $\xi$, predicted for entangled HEC solutions (A), and agarose gels (B) as a function of mesh-forming polymer volume fraction, $\Phi$.

Using this value for a, it is interesting to compare the approximate mesh sizes of the polymer solutions with those of traditional electrophoresis gels. Righetti [24]

has developed an empirical relationship to correlate mesh size in agarose gels with agarose concentration, $$\xi = 1407 C^{-0.7} \tag{14}$$

where $\xi$ is the measured mesh size (in Å) and C is the concentration of agarose (in wt%). Note that this empirical expression has the same form and a value of the exponent similar to that predicted by entanglement theory. However, comparing the results of Eqs. (2) and (14), the entangled solution appears to produce a smaller mesh size at a given weight fraction of polymer. This is consistent with the fact that in an agarose gel, the polymer fibers exist as bundles, therefore leaving larger voids. FIG. 7 compares the predicted mesh size using Eqs. (2) and (14). Thus, based on these equations, it appears that the mesh sizes achievable using entangled polymers are an order of magnitude smaller than those using agarose gels at the same polymer concentration.

EXAMPLE 3

DNA Fragment Separation in HEC Polymer Solutions

Figure 8:
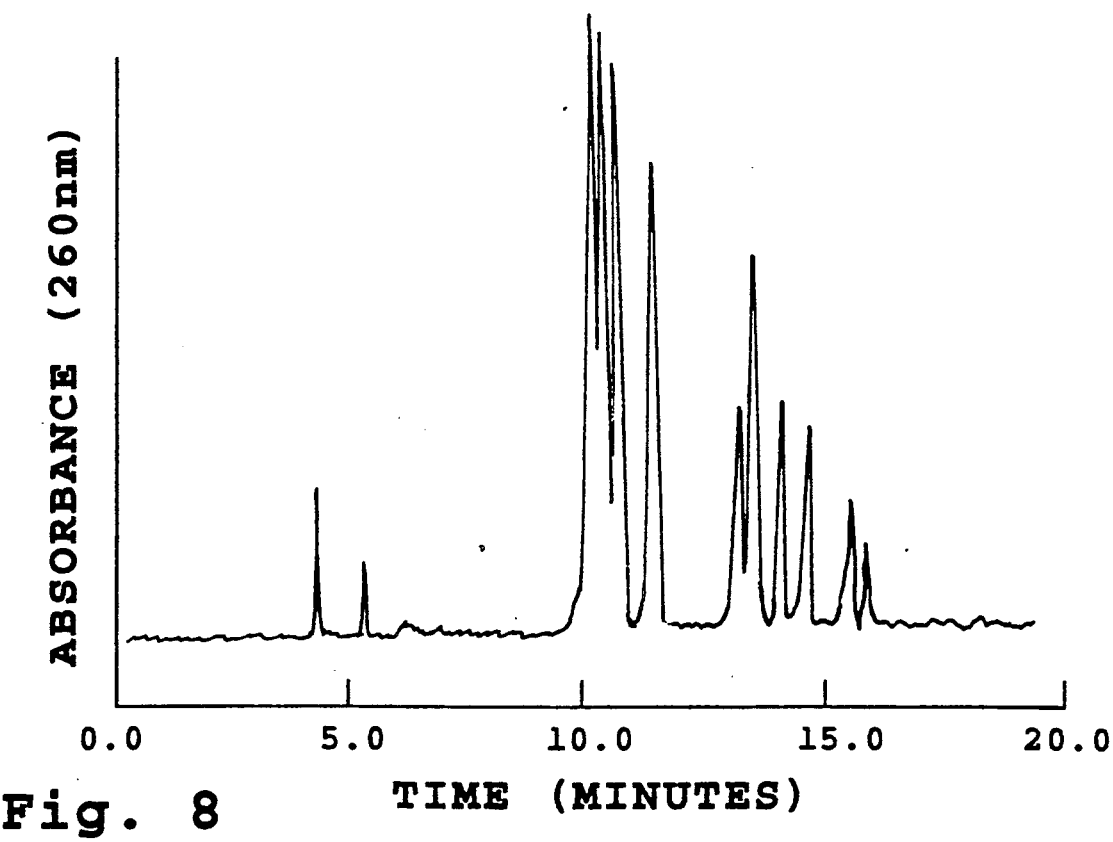
FIG. 8 is a representative electropherogram showing the separation of 11 DNA restriction fragments ranging in size from 72 to 1353 base pairs, as identified in the figure.

FIG. 8 shows a representative electropherogram of DNA fragments ranging in size from 72 to 1353 base pairs. A description of the capillary electrophoresis apparatus used in these studies as well as the methods used to calculate electrophoretic mobilities is provided elsewhere [18].

Figure 9:
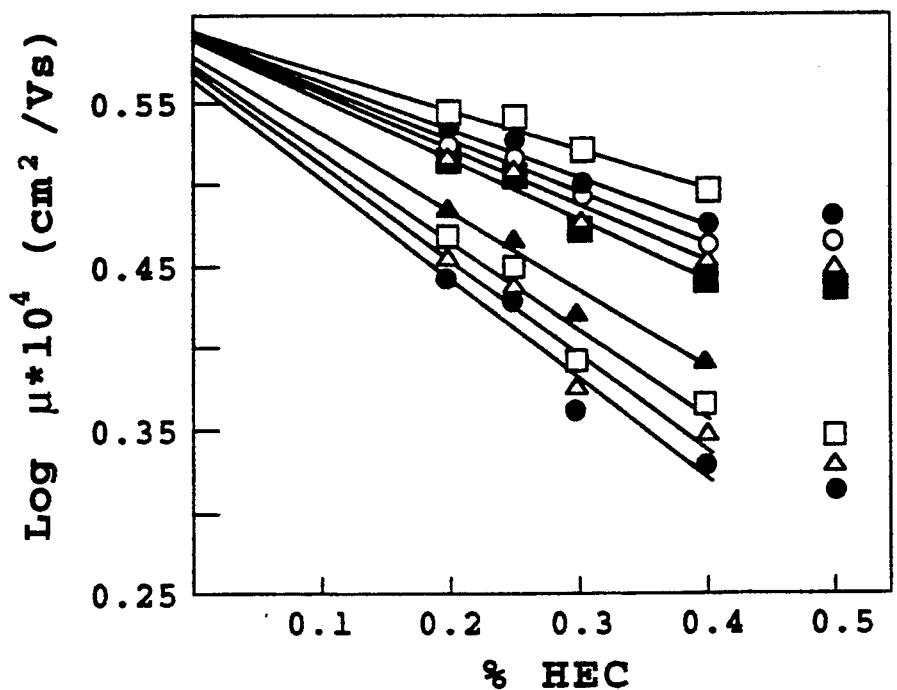
FIG. 9 is a Ferguson plot for sample DNA fragments having the identified basepair sizes between 118 and 1353 bp.

As previously stated, according to the Ogston model, a plot of log $\mu$ vs. % HEC (a Ferguson plot) should give a linear relationship with a slope equal to K, and a Y-intercept equal to log $\mu_0$. For fragments 118, 194, 234, 281, and 310 in solutions up to $\Phi^*\text{HEC}=0.4\%$, this behavior is indeed observed (FIG. 9). The intercept for these five lines, 0.588 (% RSD=0.15%), implies a value for $\mu_0$ of $3.87*10^{-4}\text{cm}^2/\text{V}$ s (% RSD=1.2%, n=16). This is an interesting result. Previously in rigid-gel systems, the value of $\mu_0$ can be measured directly, the value of $\mu_0$ could only be inferred based on the Y-intercept of the Ferguson plot. Here, because $\mu_0$ can be measure directly, the value of $\mu_0$ based on the Y-intercept can be compared with the actual measured value. The close agreement of these two values of $\mu_0$ is compelling verification of the Ogston mechanism. For fragments larger than 310 bp, the agreement degrades. This is probably due to the gradual transition to the reptation regime for these larger fragments. This transition has also been observed in agarose gels [14].

Figure 10:
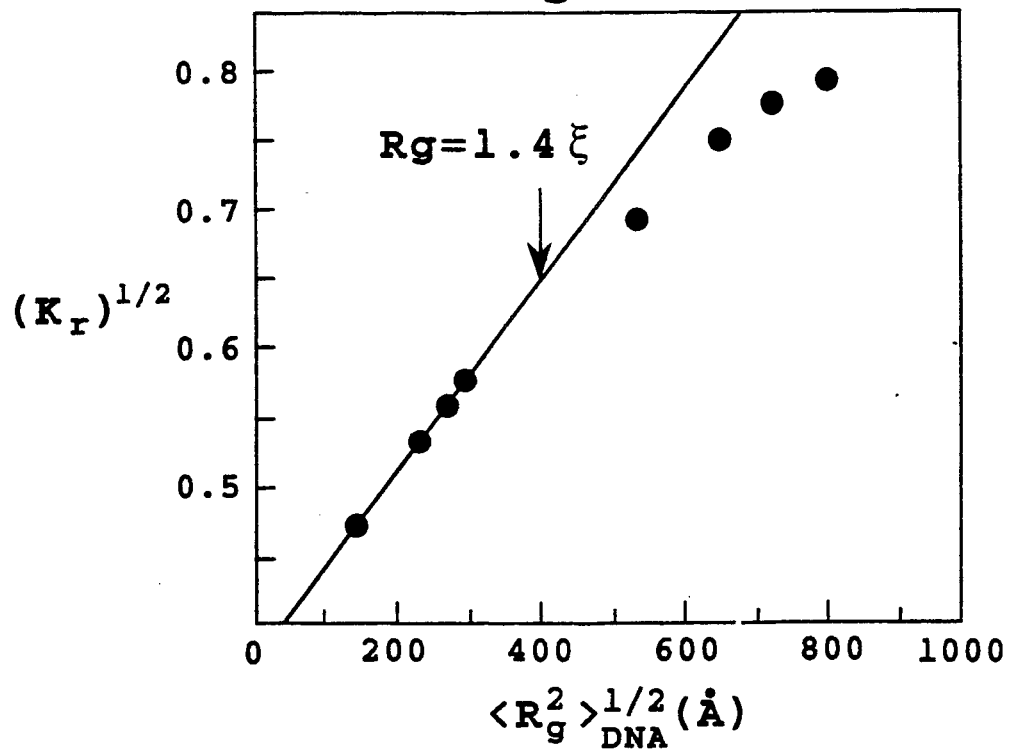
FIG. 10 shows the square root of the retardation coefficient $K_r$ vs. the root-mean-square radius of gyration $<R_g^2>^{\frac{1}{2}}$ of the DNA fragments from FIG. 9.

According to the Ogston model, a plot of $K_r^{0.5}$ vs $R_g$ should yield a linear relationship, assuming $R_g >> r$. As seen in FIG. 10, for the smaller fragments, agreement with the prediction of the Ogston model is close, while the larger fragments deviate significantly. $<R_g^2>^{\frac{1}{2}}$ is calculated for DNA using the Porod-Kratky stiff-chain model assuming a persistence-length of 450Å and a contour-length of 3.4Å per base pair [25]. According to Slater and Noolandi [26,27], based on experiments and numerical stimulations, the transition from the Ogston to the reptation regime takes place when $R_g \approx 1.4\xi$. Therefore, given that according to FIG. 10 the transition occurs when $312\text{Å} < R_g < 490\text{Å}$ and $\Phi^*_{HEC}=0.4\%$, FIG. 10 implies that when $\Phi^*_{HEC}=0.4\%$, $223\text{Å} < \xi < 350\text{Å}$. This agrees with the mesh size predicted using Eq. (2) of 264Å. Thus FIG. 10 provides an independent confirmation of Eq. (2).

Figure 11:
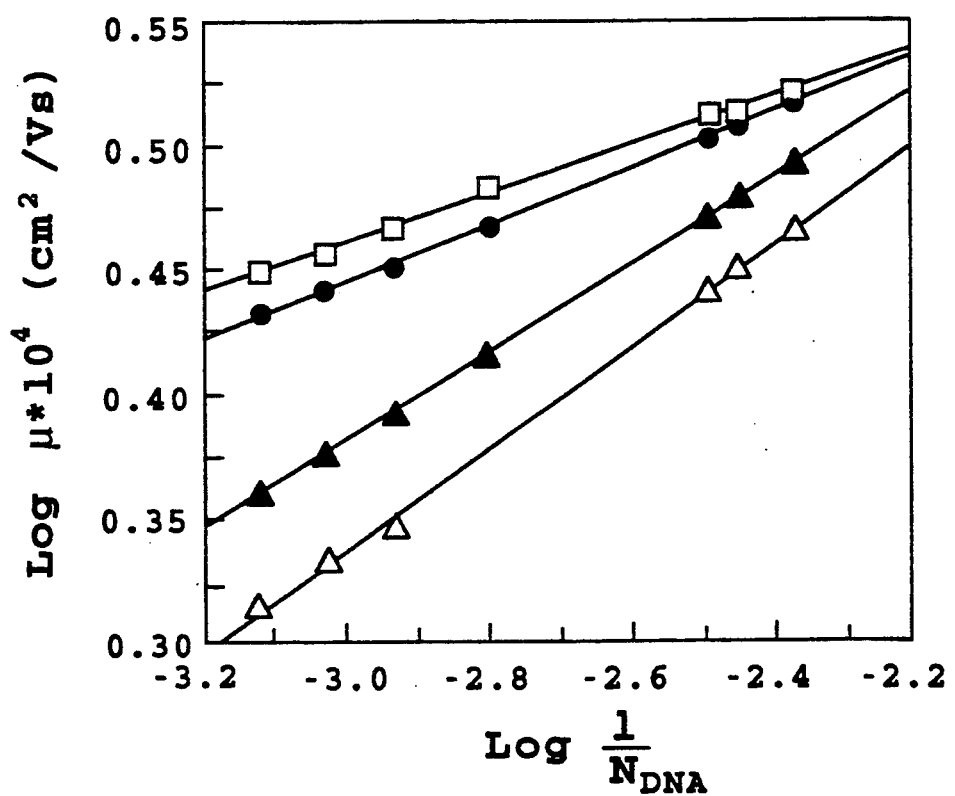
FIG. 11 is a plot of log of the electrophoretic mobility vs. log of inverse molecular size (in base pairs) for different HEC concentrations.

FIG. 11 shows a plot of log $\mu$ as a function of 1/NDNA. According to Eq. (8), these curves should be linear with slopes of 1.0 if the fragments migrate by the reptation mechanism. As expected from the previous analysis, for the conditions used in these experiments none of the curves adhere to the reptation behavior. However, as the HEC concentration is increased, the slopes of the curves appear to increase towards 1. Again, this behavior has been observed for low-concentration agarose gels using small DNA fragments [14].

It is likely that once $R_g >> \xi$, i.e. when reptation becomes important, the separation performance of these systems will decrease rapidly. This is because at the high electrical fields typically employed in capillary electrophoresis, the value of the term bE in Eq. (9) is large, resulting in a saturated, size independent mobility. Although this limitation is not unique to the polymer solution system, it does represent a restriction on the ability to exploit the high electric fields and thus enjoy the consequent rapid analysis using CE.

Although the invention has been described with respect to particular polymer solutions and applications, it will be appreciated that various changes and modifications can be made within the scope of the invention.

It is claimed:

1. A capillary electrophoresis element comprising a capillary electrophoresis tube, and
contained within the tube, a solution of an uncharged, water-soluble polymer characterized by:
   (a) a polymer mass concentration C which is between about $1/[\eta]$ and $5[\eta]$ where $[\eta]$ is the intrinsic viscosity of the polymer;
   (b) an actual solution viscosity less than about 100 centipoise; and
   (c) a polymer mesh size $\xi$ which is approximately equal to $aC^{-0.75}$, where a is the persistence length of the polymer.

2. The element of claim 1, wherein the mesh size $\xi$ is between about 50 and 100 Å, the mass concentration of the polymer is between about 3 and 6 weight percent, and the polymer solution has a viscosity between about 5 and 50 centipoise.

3. The element of claim 1, wherein the mesh size $\xi$ is between about 200 and 300 Å, the mass concentration of the polymer is between about 0.2 and 0.6 weight percent, and the polymer solution has a viscosity between about 1 and 10 centipoise.

4. A method of preparing a polymer element for use in electrophoretically separating, by capillary electrophoresis, a mixture of biopolymer molecules within a selected size range, comprising
selecting a polymer mesh size $\xi$ suitable for separating the biopolymer mixture, in an electric field,
selecting an uncharged, water-soluble polymer having an intrinsic viscosity $[\eta]$ and a persistence length a, such that the selected mesh size is approximately equal to $aC^{-0.75}$, where C is between about $1/[\eta]$ and $5/[\eta]$, and the actual viscosity is less than about 100 centipoise,
forming a solution of the polymer at a concentration C between about $1//[\eta]$ and $5/[\eta]$, and
drawing the polymer solution into a capillary electrophoresis tube.

5. The method of claim 4, wherein the mesh size $\xi$ is between about 50 and 100 Å, the mass concentration of the polymer is between about 3 and 6 weight percent, and the polymer solution has a viscosity between about 5 and 50 centipoise.

6. The method of claim 4, wherein the mesh size $\xi$ is between about 200 and 300 Å, the mass concentration of the polymer is between about 0.2 and 0.6 weight percent, and the polymer solution has a viscosity between about 1 and 10 centipoise.

* * * * *

UNITED STATES PATENT AND TRADEMARK OFFICE
CERTIFICATE OF CORRECTION

PATENT NO. : 5,126,021
DATED : June 30, 1992
INVENTOR(S) : Paul D. Grossman

It is certified that error appears in the above-indentified patent and that said Letters Patent is hereby corrected as shown below:

Column 2, line 54, delete "1[$\eta$] and 5[$\eta$] " and insert -- 1/[$\eta$] and 5/[$\eta$] --

Column 3, lines 15 and 17 (two occurrences), delete "1//[$\eta$]" and insert -- 1/[$\eta$] --.

Column 7, line 30, delete "1//[$\eta$]" and insert -- 1/[$\eta$] --.

Column 8, line 48, delete "5[$\eta$]" and insert -- 5/[$\eta$] --.

In Claim 1 at column 12, line 25, delete "5[$\eta$]" and insert -- 5/[$\eta$] --.

In Claim 4 at column 12, line 55, delete "1//[$\eta$]" and insert -- 1/[$\eta$] --.

Signed and Sealed this

Tenth Day of May, 1994

Attest:

*Attesting Officer*

BRUCE LEHMAN

*Commissioner of Patents and Trademarks*